(12) United States Patent
Goulko (10) Patent No.: US 7,993,330 B2
(45) Date of Patent: Aug. 9, 2011

(54) METHOD FOR REJUVENATING AND TIGHTENING HUMAN SKIN UTILIZING A CRYOGENIC APPLICATOR

(76) Inventor: Olga Goulko, Fort Lee, NJ (US)

( * ) Notice: Subject to any disclaimer, the term of this patent is extended or adjusted under 35 U.S.C. 154(b) by 0 days.

(21) Appl. No.: 12/806,664

(22) Filed: Aug. 18, 2010

(65) Prior Publication Data

US 2010/0318076 A1    Dec. 16, 2010

Related U.S. Application Data

(62) Division of application No. 11/432,244, filed on May 11, 2006, now Pat. No. 7,799,018.

(60) Provisional application No. 60/757,102, filed on Jan. 6, 2006.

(51) Int. Cl.
*A61B 18/02*    (2006.01)

(52) U.S. Cl. ................. 606/20; 606/22; 606/23; 606/26

(58) Field of Classification Search .............. 606/20–26; 607/104–105, 107–109
See application file for complete search history.

(56) References Cited

U.S. PATENT DOCUMENTS

| 4,074,717 | A | | 2/1978 | Schulze | |
|---|---|---|---|---|---|
| 4,082,096 | A | * | 4/1978 | Benson | ........................... 606/23 |
| 5,330,745 | A | | 7/1994 | McDow | |
| 6,273,884 | B1 | * | 8/2001 | Altshuler et al. | ................. 606/9 |
| 6,306,119 | B1 | * | 10/2001 | Weber et al. | .................. 604/290 |
| 6,350,276 | B1 | | 2/2002 | Knowlton | |
| 6,726,693 | B2 | | 4/2004 | Weber | |
| 6,749,624 | B2 | | 6/2004 | Knowlton | |
| 6,764,493 | B1 | | 7/2004 | Weber | |
| 2003/0100936 | A1 | * | 5/2003 | Altshuler et al. | ............... 607/96 |
| 2005/0249541 | A1 | * | 11/2005 | Habatjou | ...................... 401/220 |

FOREIGN PATENT DOCUMENTS

EP            1593363      * 11/2005

* cited by examiner

*Primary Examiner* — Linda C Dvorak
*Assistant Examiner* — Jaymi Della
(74) *Attorney, Agent, or Firm* — I. Zborovsky (57) ABSTRACT

A method for tightening and rejuvenating skin utilizing a cryogenic applicator, which includes the steps of holding a handle of a barrel of the cryogenic applicator in a hand, fluidly communicating the barrel with a source of a biocompatible non-toxic cryogenic fluid to supply the biocompatible non-toxic cryogenic fluid through a hollow interior of the barrel, out through a plurality of openings in a distal portion of the barrel, and onto a head of the cryogenic applicator, rolling the head quickly, smoothly, and evenly over the skin being treated for a period of time in an order of hundredths or tenths of a second, and sparging the biocompatible non-toxic cryogenic fluid onto the skin quickly, evenly, and smoothly when the head is rolled on the skin, and thereby tightening and rejuvenating the skin.

9 Claims, 6 Drawing Sheets

METHOD FOR REJUVENATING AND TIGHTENING HUMAN SKIN UTILIZING A CRYOGENIC APPLICATOR

1. CROSS REFERENCE TO RELATED APPLICATIONS

The instant non-provisional patent application is a divisional patent application of non-provisional patent application Ser. No. 11/432,244, filed on May 11, 2006 now U.S. Pat. No. 7,799,018, for a CRYOGENIC APPLICATOR FOR REJUVENATING SKIN AND A METHOD FOR USING THE APPLICATOR, which claims priority from provisional patent application 60/757,102 filed on Jan. 6, 2006, entitled CRYOGENIC APPLICATOR AND RELATED SKIN TREATMENT, and which both are incorporated herein by reference thereto.

2. BACKGROUND OF THE INVENTION

A. Field of the Invention.

An embodiment of the present invention relates to a method for rejuvenating and tightening human skin, and more particularly, to a method for rejuvenating and tightening human skin utilizing a cryogenic applicator.

B. Description of the Prior Art.

Liquid nitrogen, and/or other biocompatible non-toxic cryogenic liquids, all herein sometimes referred to as "cryogenic liquids" is frequently used at offices of physicians in removal of warts, lesions, sun damage, and/or the like from a person's skin. For example, a method used for removing a wart is to apply liquid nitrogen thereto for a substantial length of time, usually a matter of seconds. The liquid nitrogen has a boiling temperature of approximately $-335°$ F.

Although liquid nitrogen is here mentioned, it will be understood that other suitable biocompatible non-toxic cryogenic liquids could be substituted therefor, and the very cold temperature used in the treatment could be different and might vary. In treating the wart, the nitrogen "burns" by freezing the wart.

Numerous innovations for skin rejuvenation have been provided in the prior art, which will described below in chronological order to show advancement in the art, and which are incorporated herein by reference thereto. Even though each of these innovations may be suitable for a specific purpose to which it is addressed, the innovations all differ in structure and/or technique and/or objective from that of the present invention, in that they do not teach a method for rejuvenating and tightening human skin utilizing a cryogenic applicator.

(1) U.S. Pat. No. 4,074,717 to Schulze et al.

U.S. Pat. No. 4,074,717 issued to Schulze et al. on Feb. 21, 1978 teaches a cryogenic probe, its method of charging, and its method of use. The probe includes a barrel having a plunger mechanism movably mounted therein and a valve on the lower end thereof. The valve normally closes the lower end of the barrel, but the plunger is movable relative to the barrel to permit a cryogenic liquid, such as liquid nitrogen, to by-pass the valve and move upwardly into the interior of the barrel. The valve has a tip portion at the lower end thereof. The barrel is removably positioned in a guard, so that the tip portion extends outwardly through the bottom of the guard, whereby the upper end of the plunger is exposed above the guard. The tip portion has a lower end portion that is extremely thin, so that the cryogenic liquid will be positioned closely adjacent the skin, but not in actual contact therewith when the tip portion is placed into contact with the patient's skin.

(2) U.S. Pat. No. 5,330,745 to McDow.

U.S. Pat. No. 5,330,745 issued to McDow on Jul. 19, 1994 teaches a method for cryogenically treating a skin lesion employing a hollow fluid retaining device for retaining cryogenic refrigerant in a liquid pool, and then contacting the area of the skin lesion at a temperature and for a time, so that permanent, irreversible rupture of the cellular membrane of the lesion cells occurs.

(3) U.S. Pat. No. 6,350,276 to Knowlton.

U.S. Pat. No. 6,350,276 issued to Knowlton on Feb. 26, 2002 teaches a fluid delivery apparatus for introducing a fluid cooling media to a skin surface, including a template with a skin interface surface. An energy delivery device is coupled to the template. A fluid cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

(4) U.S. Pat. No. 6,726,693 to Weber et al.

U.S. Pat. No. 6,726,693 issued to Weber et al. on Apr. 27, 2004 teaches tissue resurfacing accomplished by propelling biocompatible, non-toxic materials at the tissue with sufficient velocity to cause destruction or loosening of tissues to a desired depth. The biocompatible materials are generated by abrading a solid frozen unit and propelling the abraded material onto the surface of the skin or tissue to be treated. A vacuum line near the delivery tip is used to remove excess materials or reaction by-products building up on the surface of the skin. The treatment system generally includes a control unit, a handheld particle generator, and a cable connecting the control unit to the particle generator. The control unit includes user controls to select particle temperature, particle flux, particle velocity, and vacuum. The handheld particle generator contains a mechanism to push the frozen biocompatible material against a rotating grinding wheel producing the small particles being propelled against tissue being treated.

(5) U.S. Pat. No. 6,749,624 to Knowlton.

U.S. Pat. No. 6,749,624 issued to Knowlton on Jun. 15, 2004 teaches a fluid delivery apparatus for introducing a fluid cooling media to a skin surface, which includes a template with a skin interface surface. An energy delivery device is coupled to the template. A fluid cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

(6) U.S. Pat. No. 6,764,493 to Weber et al.

U.S. Pat. No. 6,764,493 issued to Weber et al. on Jul. 20, 2004 teaches biocompatible materials propelled at the skin with sufficient velocity to cause desired resurfacing of tissue to the desired penetration depth. The materials, such as dry ice or water ice, are harmonious with the human body and thus eliminate foreign body reactions. Various materials are used in combination, which include local anesthetics and vasoconstrictors in solid or liquid form. The biocompatible solid or liquid particles are suspended in a cold carrier fluid, and are propelled through an insulated delivery system to the surface of the skin. The treatment of diseased skin lesions is accomplished by its use as a drug delivery system.

It is apparent that numerous innovations for skin treatments have been provided in the prior art. Even though these innovations each may be suitable for a specific purpose to which it is addressed, the innovations would not be suitable, either individually or collectively, for the purposes of an embodiment of the present invention as hereafter described, namely, a method for rejuvenating and tightening human skin utilizing a cryogenic applicator.

3. SUMMARY OF THE INVENTION

Thus, an object of an embodiment of the present invention is to provide a method for rejuvenating and tightening human skin utilizing a cryogenic applicator, which avoids the disadvantages of the prior art.

Briefly stated, another object of an embodiment of the present invention is to provide a method for tightening and rejuvenating skin utilizing a cryogenic applicator, which includes the steps of holding a handle of a barrel of the cryogenic applicator in a hand, fluidly communicating the barrel with a source of a biocompatible non-toxic cryogenic fluid to supply the biocompatible non-toxic cryogenic fluid through a hollow interior of the barrel, out through a plurality of openings in a distal portion of the barrel, and onto a head of the cryogenic applicator, rolling the head quickly, smoothly, and evenly over the skin being treated for a period of time in an order of hundredths or tenths of a second, and sparging the biocompatible non-toxic cryogenic fluid onto the skin quickly, evenly, and smoothly when the head is rolled on the skin, and thereby tightening and rejuvenating the skin.

The novel features considered characteristic of an embodiment of the present invention are set forth in the appended claims. An embodiment of the present invention itself, however, both as to its construction and its method of operation together with additional objects and advantages thereof will be best understood from the following description of an embodiments when read and understood in connection with the accompanying figures of the drawing.

4. BRIEF DESCRIPTION OF THE FIGURES OF THE DRAWING

The figures of the drawing are briefly described as follows.

5. LIST OF REFERENCE NUMERALS UTILIZED IN THE FIGURES OF THE DRAWING

A. General
10 cryogenic applicator utilized by method of embodiment of present invention for rejuvenating and tightening human skin 12
12 human skin
B. Overall Configuration of Cryogenic Applicator 10
14 barrel
15 flow-control dial of barrel 14 for controlling flow of biocompatible non-toxic cryogenic fluid 20
16 head
18 cryogenic interface for fluidly connecting barrel 14 to source 22 of biocompatible non-toxic cryogenic fluid 20 to supply cryogenic fluid 20 through barrel 14 to head 16 that in turn sparges biocompatible non-toxic cryogenic fluid 20 onto skin 12 quickly, evenly, and smoothly when head 16 is rolled on skin 12, and thereby tightening and rejuvenating skin 12
20 biocompatible non-toxic cryogenic fluid
22 source of biocompatible non-toxic cryogenic fluid 20
C. Specific Configuration of Barrel 14, Head 16, and Cryogenic Interface 18
23 hollow interior of barrel 14 for directing biocompatible non-toxic cryogenic liquid 20 to head 16.
24 proximal portion of barrel 14
26 distal portion of barrel 14
28 handle of proximal portion 24 of barrel 14 for being hand-held
30 plurality of openings in distal portion 26 of barrel 14
32 circumferential groove in barrel 14
34 end of distal portion 26 of barrel 14
36 tit of end 34 of distal portion 26 of barrel 14
38 flexible tube of cryogenic interface 18 for fluidly communicating with source 22 of cryogenic fluid 20 to supply cryogenic fluid 20 through hollow interior 23 of barrel 14, out through plurality of openings 30 in distal portion 26 of barrel 14, and onto head 16 that in turn sparges cryogenic fluid 20 onto skin 12 quickly, evenly, and smoothly when head 16 is rolled on skin 12, and thereby tightening and rejuvenating the skin 12
39 valve for regulating flow of cryogenic fluid
40 drum of head 16
42 web of head 16
44 mesh of drum 40 of head 16
46 soft porous material of web 42 of head 16 for contacting skin 12 in rolling action
48 proximal end of mesh 44 of drum 40 of head 16
50 distal end of mesh 44 of drum 40 of head 16
52 circumferential ring of proximal end 48 of mesh 44 of drum 40 of head 16
54 opening in distal end 50 of mesh 44 of drum 40 of head 16

6. DETAILED DESCRIPTION OF AN EMBODIMENT

A. General

Figure 1:
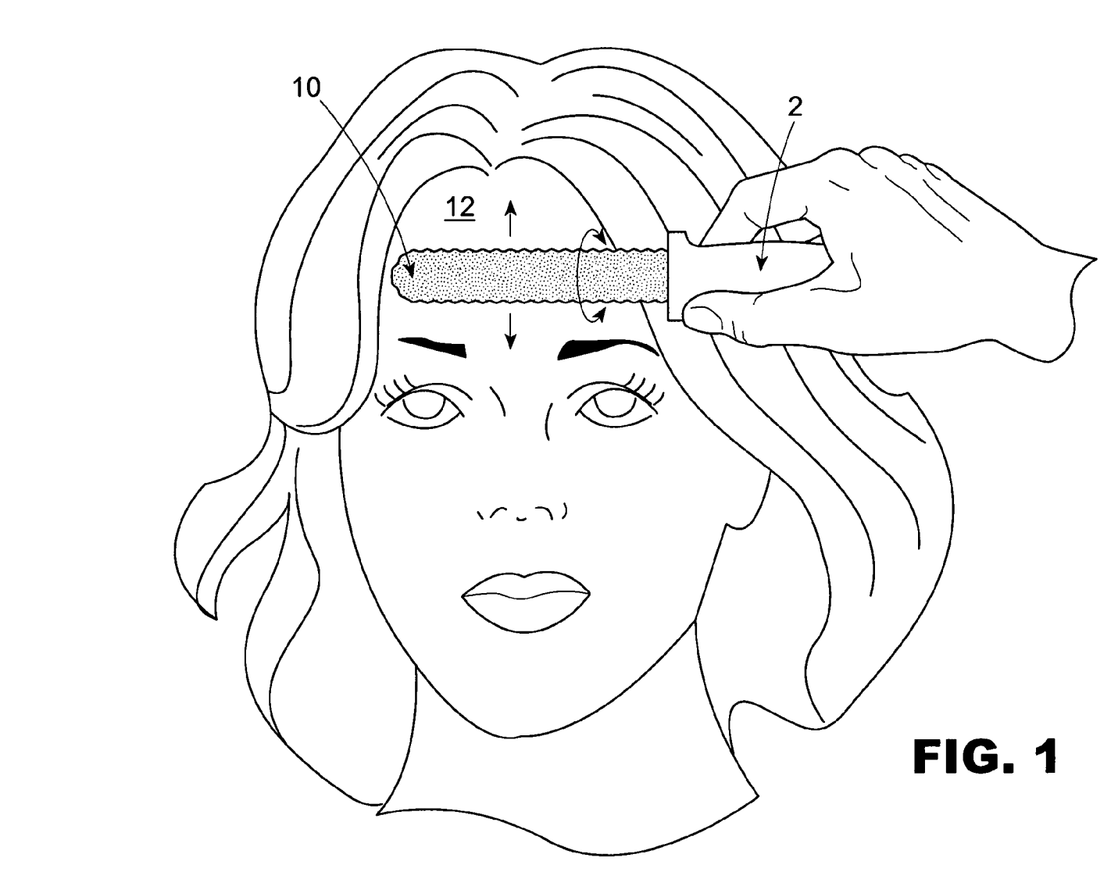
FIG. 1 is a diagrammatic perspective view of the cryogenic applicator utilized by an embodiment of the method of the present invention.

Referring now to the figures, in which like numerals indicate like parts, and particularly to FIG. 1, a diagrammatic perspective view of the cryogenic applicator utilized by an embodiment of the method of the present invention, the cryogenic applicator utilized by the method of an embodiment of the present invention is shown generally at 10 for rejuvenating and tightening human skin 12.

B. Overall Configuration of the Cryogenic Applicator 10

The overall configuration of the cryogenic applicator 10 can best be seen in FIG. 2, which is an enlarged diagrammatic perspective view of the cryogenic applicator utilized by an embodiment of the method of the present invention identified by ARROW 2 in FIG. 1, and as such, will be discussed in conjunction therewith. The cryogenic applicator 10 comprises a barrel 14, a head 16, and a cryogenic interface 18.

The barrel 14 is hand-held, and is provided with a flow-control dial 15.

The head 16 is rotatably mounted to the barrel 14.

The cryogenic interface 18 is for fluidly connecting the barrel 14 to a source 22 of a biocompatible non-toxic cryogenic fluid 20 to supply the cryogenic fluid 20 through the barrel 14 to the head 16 that in turn sparges the biocompatible non-toxic cryogenic fluid 20 onto the skin 12 quickly, evenly, and smoothly when the head 16 is rolled on the skin 12, and thereby tightening and rejuvenating the skin 12.

The valve 39, or similar apparatus for controlling flow of the cryogenic liquid can be arranged, as is well known in the art, at the source 22, in the interface 18, or at the barrel 14. The valve 39, or similar apparatus, is controllable by the operator by way of the dial 15 using ways also well known in the art.

The cryogenic applicator 10 provides a simple, effective way for wrinkle, lesion, and discoloration reduction or elimination thereof from the skin 12. Applicant achieves tightening and rejuvenation of the skin 12 by using a quick, smooth, and even application of the cryogenic fluid 20, e.g., liquid nitrogen or other suitable biocompatible non-toxic cryogenic liquid, over one or more substantial surfaced areas of a person's skin 12.

Typically, the areas of the skin 12 treated include the forehead, the temples, the nose, the cheeks, around the eyes, the cheeks, the chin, the neck, the backs of the hands, and/or other suitable areas for a dramatically shorter time period, typically in the order of hundredths or tenths of a second, so that the cryogenic liquid 20 quickly evaporates, wrinkles, lesions, and discolorations are reduced or eliminated, and the skin 12 is tightened and rejuvenated.

These things happen while the person experiences mild exhilaration. The treatment is painless, eliminating a need for local anesthetic, in fact it is a pleasurable experience. It affects only the epidermal layer(s) of the skin 12 because the cryogenic liquid 20 is applied at its boiling temperature for a very short length of time, so that damage to the epidermal layer does not occur.

With proper operation of the cryogenic applicator 10, heat of the skin 12 very quickly evaporates the cryogenic liquid 20 in at the most one to two seconds to treat wrinkles, blemishes, and/or discolorations without adversely affecting the skin 12. Waste of the biocompatible non-toxic cryogenic liquid 20 is avoided eliminating a need for expensive facilities for storage thereof. The cryogenic applicator 10 is economical to manufacture, reliable, durable, easy and safe to use, refined in appearance, easy to clean, and easy to maintain.

C. Specific Configuration of the Barrel 14, the Head 16, and the Cryogenic Interface 18

Figure 2:
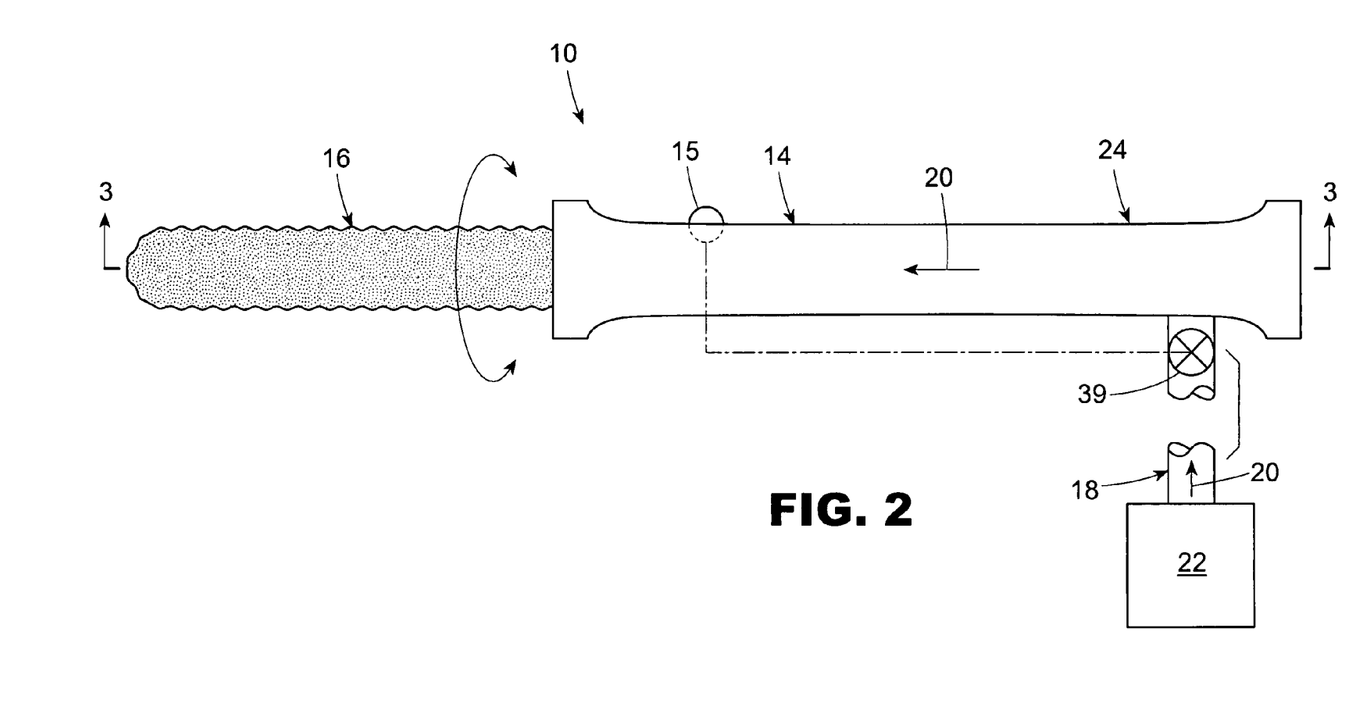
FIG. 2 is an enlarged diagrammatic perspective view of the cryogenic applicator utilized by an embodiment of the method of the present invention identified by ARROW 2 in FIG. 1.
Figure 3:
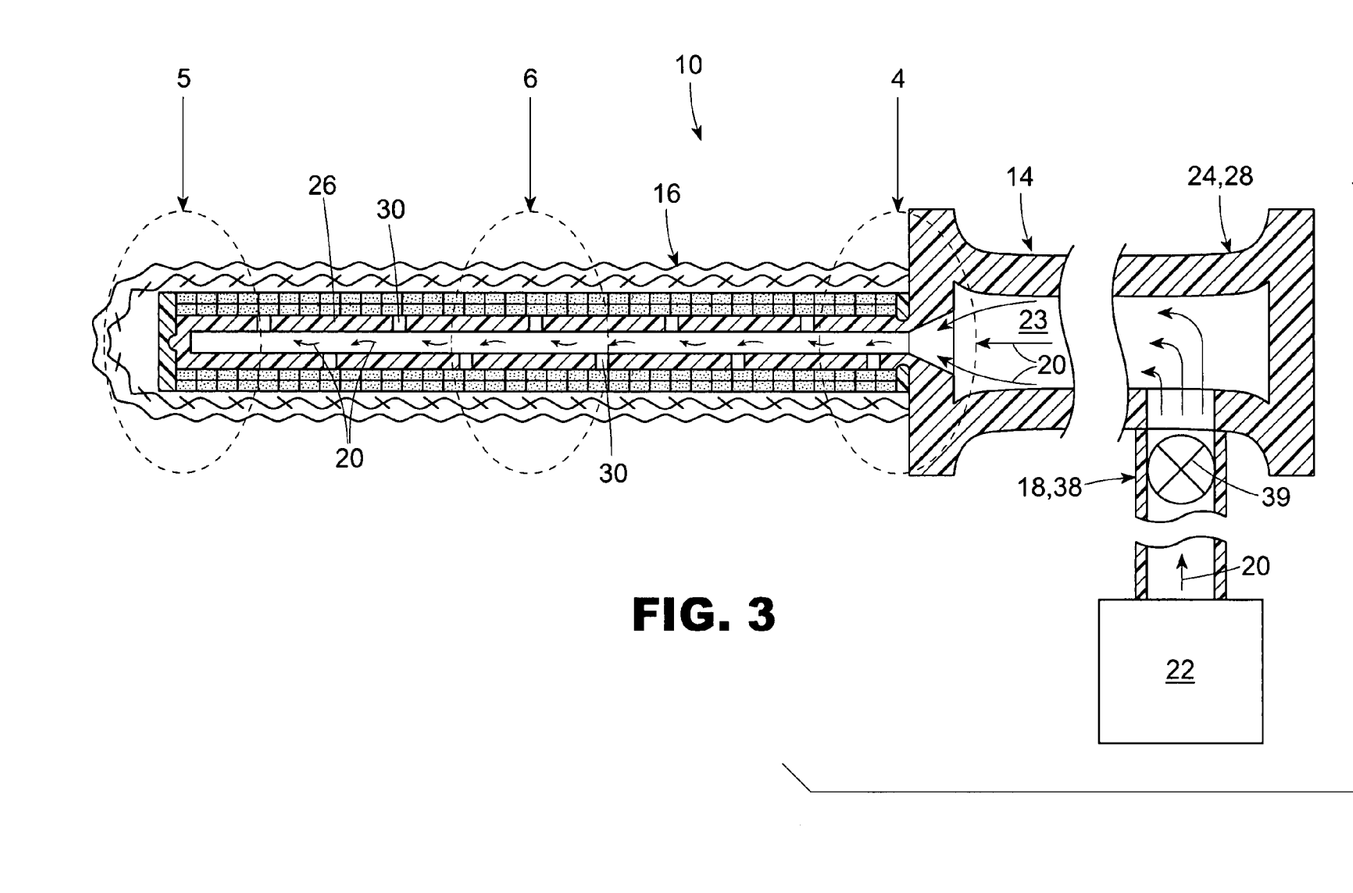
FIG. 3 is an enlarged diagrammatic cross sectional view taken along LINE 3-3 in FIG. 2.

The specific configuration of the barrel 14, the head 16, and the cryogenic interface 18 can best be seen in FIGS. 3-6, which are, respectively, an enlarged diagrammatic cross sectional view taken along LINE 3-3 in FIG. 2, an enlarged diagrammatic cross sectional view of the area generally enclosed by the dotted curve identified by ARROW 4 in FIG. 3, an enlarged diagrammatic cross sectional view of the area generally enclosed by the dotted curve identified by ARROW 5 in FIG. 3, and an enlarged diagrammatic cross sectional view of the area generally enclosed by the dotted curve identified by ARROW 6 in FIG. 3, and as such, will be discussed with reference thereto.

The barrel 14 is slender, elongated, and has a hollow interior 23, a proximal portion 24, and a distal portion 26.

The hollow interior 23 of the barrel 14 is for directing the biocompatible non-toxic cryogenic liquid 20 to the head 16.

The proximal portion 24 of the barrel 14 functions as a handle 28 for being hand-held.

The distal portion 26 of the barrel 14 has a plurality of openings 30 extending radially therethrough, spaced axially therealong, and communicating with the hollow interior 23 of the barrel 14 for passing the biocompatible non-toxic cryogenic liquid 20 to the head 16.

The source of the cryogenic fluid 20 could be arranged optionally in the barrel 14. By this expedient, the interface (supply tube) 18 could be eliminated. The barrel 14 could be thinner and ergonomically shaped, being thinner or wider in its middle. The barrel 14 should heft like a knife handle.

Figure 4:
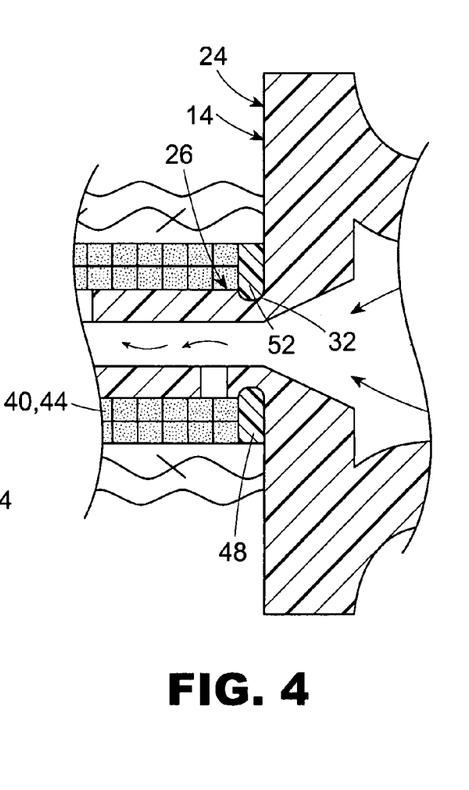
FIG. 4 is an enlarged diagrammatic cross sectional view of the area generally enclosed by the dotted curve identified by ARROW 4 in FIG. 3.

As shown in FIG. 4, the barrel 14 further has a circumferential groove 32 extending completely therearound and being located where the proximal portion 24 of the barrel 14 meets the distal portion 26 of the barrel 14.

Figure 5:
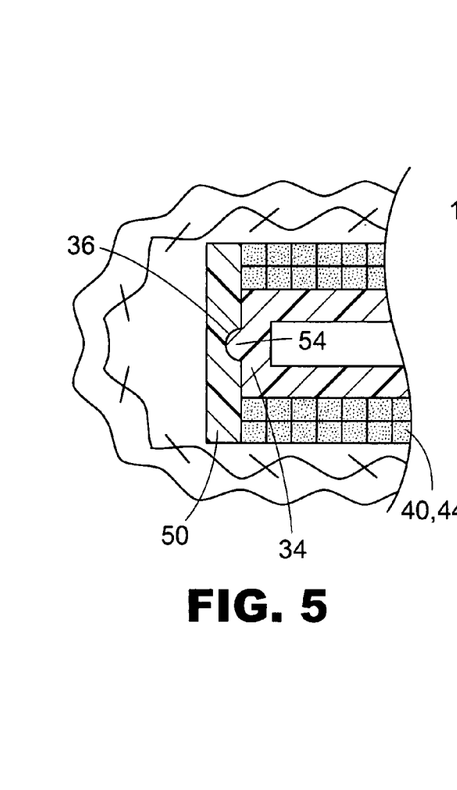
FIG. 5 is an enlarged diagrammatic cross sectional view of the area generally enclosed by the dotted curve identified by ARROW 5 in FIG. 3.

As shown in FIG. 5, the distal portion 26 of the barrel 14 terminates in an end 34. The end 34 of the distal portion 26 of the barrel 14 is closed, and has a tit 36 extending axially outwardly therefrom.

Returning now to FIG. 3, the cryogenic interface 18 is a flexible tube 38 fluidly communicating with the proximal portion 24 of the barrel 14 and for fluidly communicating with the source 22 of the cryogenic fluid 20 to supply the cryogenic fluid 20 through the hollow interior 23 of the barrel 14, out through the plurality of openings 30 in the distal portion 26 of the barrel 14, and onto the head 16 (FIG. 6) that in turn sparges the cryogenic fluid 20 onto the skin 12 quickly, evenly, and smoothly when the head 16 is rolled on the skin 12, and thereby tightening and rejuvenating the skin 12.

Figure 6:
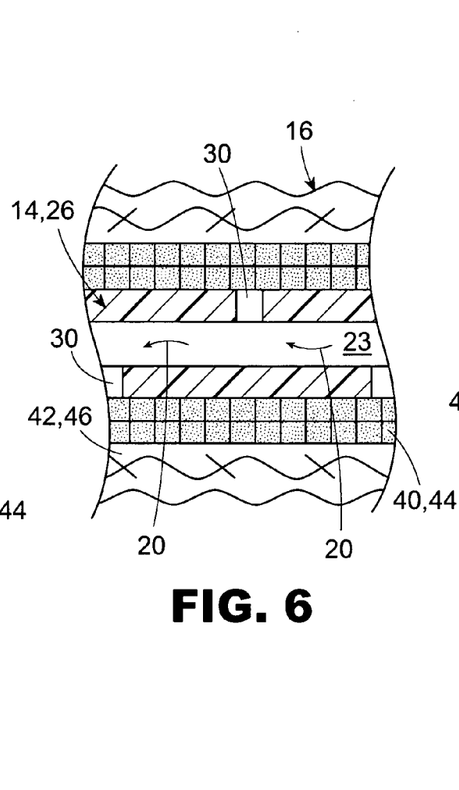
FIG. 6 is an enlarged diagrammatic cross sectional view of the area generally enclosed by the dotted curve identified by ARROW 6 in FIG. 3.

As shown in FIG. 6, the head 16 comprises a drum 40 and a web 42.

The drum 40 of the head 16 is open surfaced, such as a mesh 44, and is generally cylindrically-shaped and rotatably mounted to the distal portion 26 of the barrel 14.

The web 42 of the head 16 is a soft porous material 46, such as cotton or fabric, woven or non-woven, overlying the mesh 44 of the drum 40 of the head 16 and affixed thereto for contacting the skin 12 in a rolling action. The mesh 44 can be replaceably disposable like a sock.

The mesh 44 of the drum 40 of the head 16 provides support for the soft porous material 46 of the web 42 of the head 16, while allowing the cryogenic fluid 20 passing through the plurality of openings 30 in the distal portion 26 of the barrel 14 to pass therethrough and into the soft porous material 46 of the web 42 of the head 16 that in turn sparges the cryogenic fluid 20 onto the skin 12 quickly, evenly, and smoothly when the head 16 is rolled on the skin 12, and thereby tightening and rejuvenating the skin 12.

The mesh 44 of the drum 40 of the head 16 has a proximal end 48 (FIG. 4) and a distal end 50 (FIG. 5).

As shown in FIG. 4, the proximal end 48 of the mesh 44 of the drum 40 of the head 16 is formed into a circumferential ring 52 rotatably engaging in the circumferential groove 32 in the barrel 14, and as shown in FIG. 5, the distal end 50 of the mesh 44 of the drum 40 of the head 16 has an opening 54 therein rotatably receiving the tit 36 on the end 34 of the distal portion 26 of the barrel 14 for journaling and allowing the head 16 to rotate axially relative to the barrel 14.

It is to be understood that the positioning of the opening 54 and the tit 36 can be reversed without departing from the spirit of an embodiment of the present invention.

D. Method for Tightening and Rejuvenating the Skin 12 Utilizing the Cryogenic Applicator 10

Figure 7A:
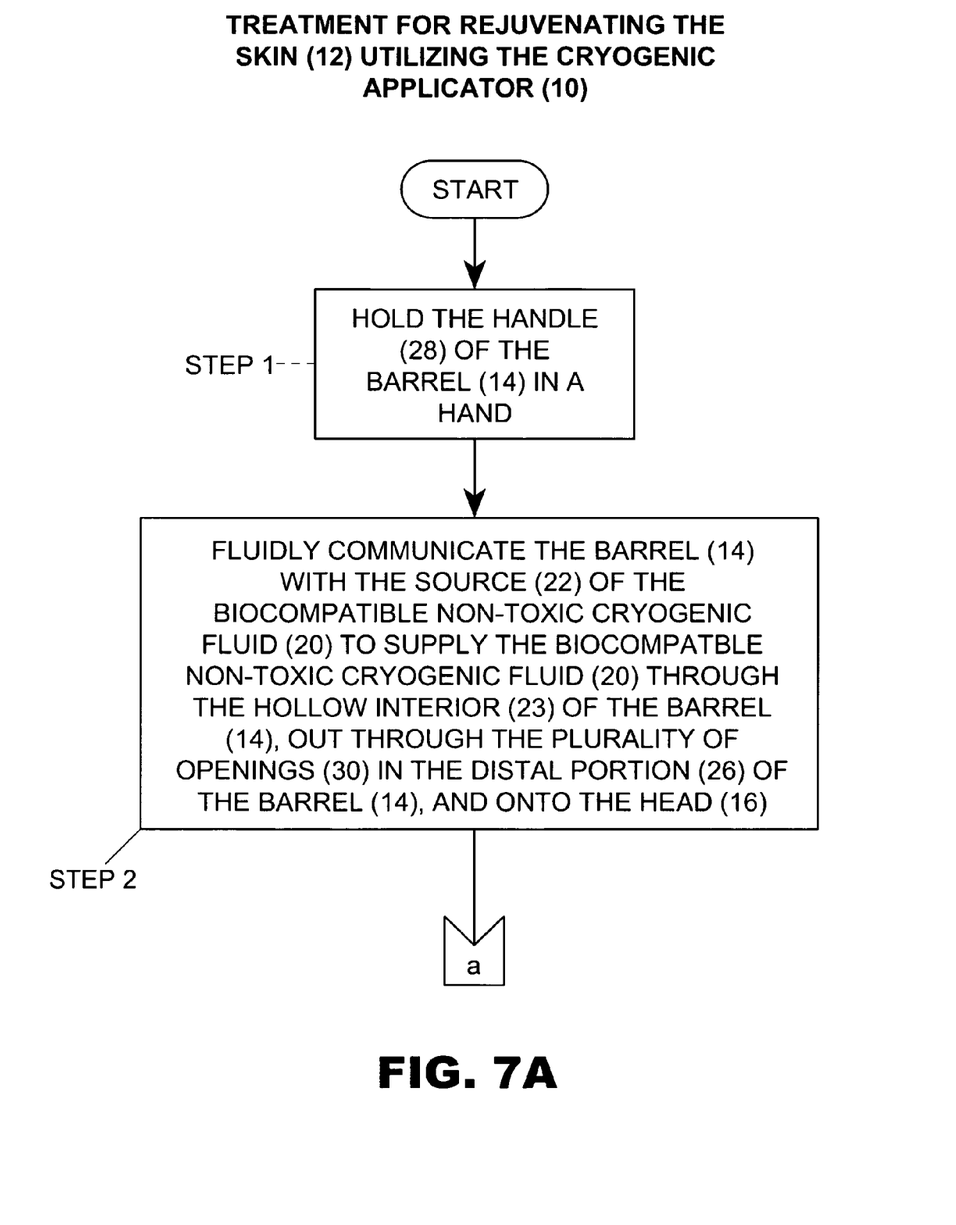
FIGS. 7A-7B are a flowchart of the method of an embodiment of the present invention.
Figure 7B:
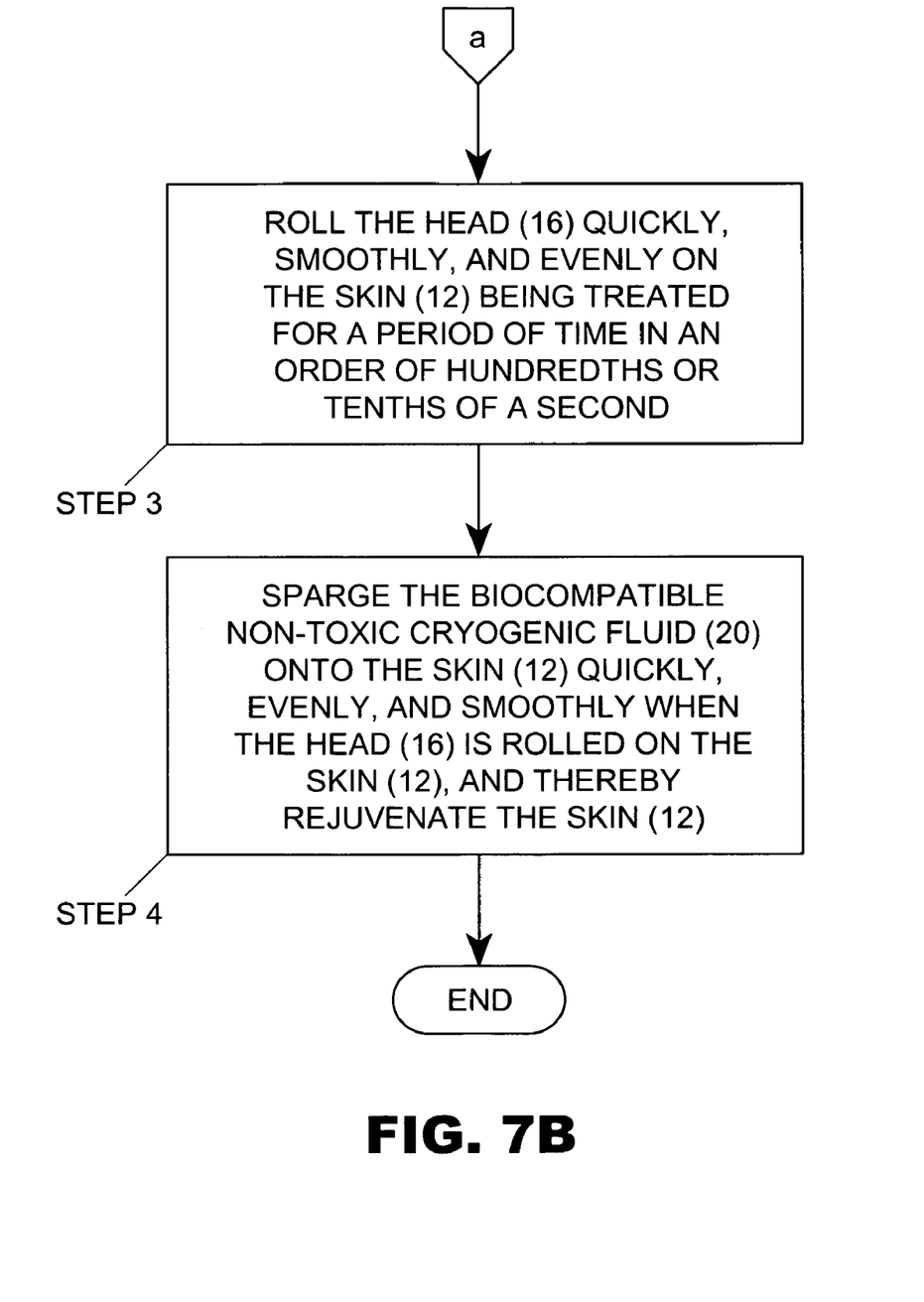

The method for tightening and rejuvenating the skin 12 utilizing the cryogenic applicator 10 can best be seen FIGS. 7A-7B, which are a flowchart of the method of an embodiment of the present invention, and as such, will be discussed with reference thereto.

STEP 1: Hold the handle 28 of the barrel 14 in a hand. The dial 15 controls flow of the cryogenic fluid 20 using the valve 39.

STEP 2: Fluidly communicate the barrel 14 with the source 22 of the cryogenic fluid 20 to supply the cryogenic fluid 20 through the interior 23 of the barrel 14, out through the plurality of openings 30 in the distal portion 26 of the barrel 14, and onto the head 16. Control flow of the cryogenic material (if necessary) by way of the dial 15.

STEP 3: Roll the head 16 quickly, smoothly, and evenly over the skin 12 being treated for a period of time of a different magnitude from typical procedures, such as "burning" of warts, more in the order of hundredths or tenths of a second.

STEP 4: Sparge the biocompatible non-toxic cryogenic fluid 20 onto the skin 12 quickly, evenly, and smoothly when the head 16 is rolled on the skin 12, and thereby tightening and rejuvenate the skin 12.

The person experiences a mild tingling and exhilarating feeling. Wrinkles, blemishes, and discolorations are reduced or eliminated. The skin 12 is stimulated and rejuvenated. The old look younger, the young look better, all look happier, their skin 12 looks refreshed, and they feel buoyant. So their usual reaction is to rejoice.

It is to be understood that some other biocompatible non-toxic cryogenic fluid 20 could be used in place of the liquid nitrogen, and the form of the handle 28 of the proximal portion 24 of the barrel 14 could be modified. Connection with the supply 22 of the cryogenic fluid 20 and its control 15 and valve 39 could take different forms. Methods of connecting the head 16 mechanically to the barrel 14 for axial rotation thereabout may vary. The materials of the barrel 14 and the head 16 could be either metal, plastic, or some combination thereof, and the cotton of the soft porous material 46 might be replaced typically by a non-woven fabric or any other suitable soft porous material.

E. Impression

It will be understood that each of the elements described above or two or more together may also find a useful application in other types of constructions differing from the types described above.

Although an embodiment of the present invention has been illustrated and described as embodied in a method for tightening and rejuvenating skin utilizing a cryogenic applicator, however, it is not limited to the details shown because it will be understood that various omissions, modifications, substitutions, and changes in the forms and details of the device illustrated and its operation can be made by those skilled in the art without departing from the spirit of an embodiment of the present invention.

Without further analysis, the foregoing will so fully reveal the gist of an embodiment of the present invention that others can by applying current knowledge readily adapt it for various applications without omitting features that from the standpoint of prior art fairly constitute characteristics of the generic or specific aspects of an embodiment of the present invention.

The invention claimed is:

1. A method for tightening and rejuvenating skin utilizing a cryogenic applicator, comprising the steps of:
    holding a handle of a barrel of the cryogenic applicator in a hand;
    fluidly communicating the cryogenic applicator with a source of a biocompatible non-toxic cryogenic fluid to supply the biocompatible non-toxic cryogenic fluid through the cryogenic applicator;
    directing, by a hollow interior of the barrel of the cryogenic applicator, the biocompatible non-toxic cryogenic liquid to a head of the cryogenic applicator;
    rolling the head of the cryogenic applicator quickly, smoothly, and evenly over the skin;
    sparging the biocompatible non-toxic cryogenic fluid onto the skin when the cryogenic applicator is being rolled, thereby tightening and rejuvenating the skin,
    wherein said fluidly communicating step includes fluidly communicating the barrel of the cryogenic applicator with the source of the biocompatible non-toxic cryogenic fluid through the hollow interior of the barrel, out through a plurality of openings in a distal portion of the barrel, the openings extending radially through said distal portion and spaced axially along said distal portion, and onto the head of the cryogenic applicator.

2. The method of claim 1, wherein said holding step includes holding the handle of the barrel of the cryogenic applicator, which has a circumferential groove extending completely therearound and being located where a proximal portion of the barrel meets the distal portion of the barrel.

3. The method of claim 2, wherein said holding step includes holding the handle of the barrel of the cryogenic applicator, the distal end of the barrel terminating in an end that is closed and has a tit extending axially outwardly therefrom.

4. The method of claim 1, wherein said fluidly communicating step includes fluidly communicating a cryogenic interface of the barrel, the cryogenic interface comprising a flexible tube that fluidly communicates with a proximal portion of the barrel with the source of the biocompatible non-toxic cryogenic fluid to supply the biocompatible non-toxic cryogenic fluid through the hollow interior of the barrel, out through the plurality of openings in the distal portion of the barrel, and onto the head that sparges the biocompatible non-toxic cryogenic fluid onto the skin quickly, evenly, and smoothly when the head is being rolled on the skin.

5. The method of claim 1, wherein said fluid communicating step includes supplying the biocompatible non-toxic cryogenic fluid onto the head of the cryogenic applicator, the head comprising a drum and a web.

6. The method of claim 5, wherein said fluid communicating step includes supplying the biocompatible non-toxic cryogenic fluid through a hollow interior of a barrel onto the head of cryogenic applicator, wherein the drum is open surfaced, generally cylindrically shaped, and rotatably mounted to the distal portion of the barrel.

7. The method of claim 1, wherein said fluid communicating step includes supplying the biocompatible non-toxic cryogenic fluid onto the head of the cryogenic applicator, which has a drum that is a mesh.

8. The method of claim 1, wherein said fluid communicating step includes supplying the biocompatible non-toxic cryogenic fluid onto the head of the cryogenic applicator, the head comprising a web that is a soft porous material that overlies a mesh of a drum of the head, wherein the web is affixed to the mesh of the drum of the head and contacts the skin when the head is being rolled.

9. The method of claim 7, wherein said fluid communicating step includes supplying the biocompatible non-toxic cryogenic fluid onto the head of the cryogenic applicator, which has a web that is a soft porous material that is selected from the group consisting of cotton, fabric, woven, and non-woven.

\* \* \* \* \*